July 20, 1965 C. SAMTMANN Plant Pat. 2,545
ROSE PLANT
Filed April 20, 1964
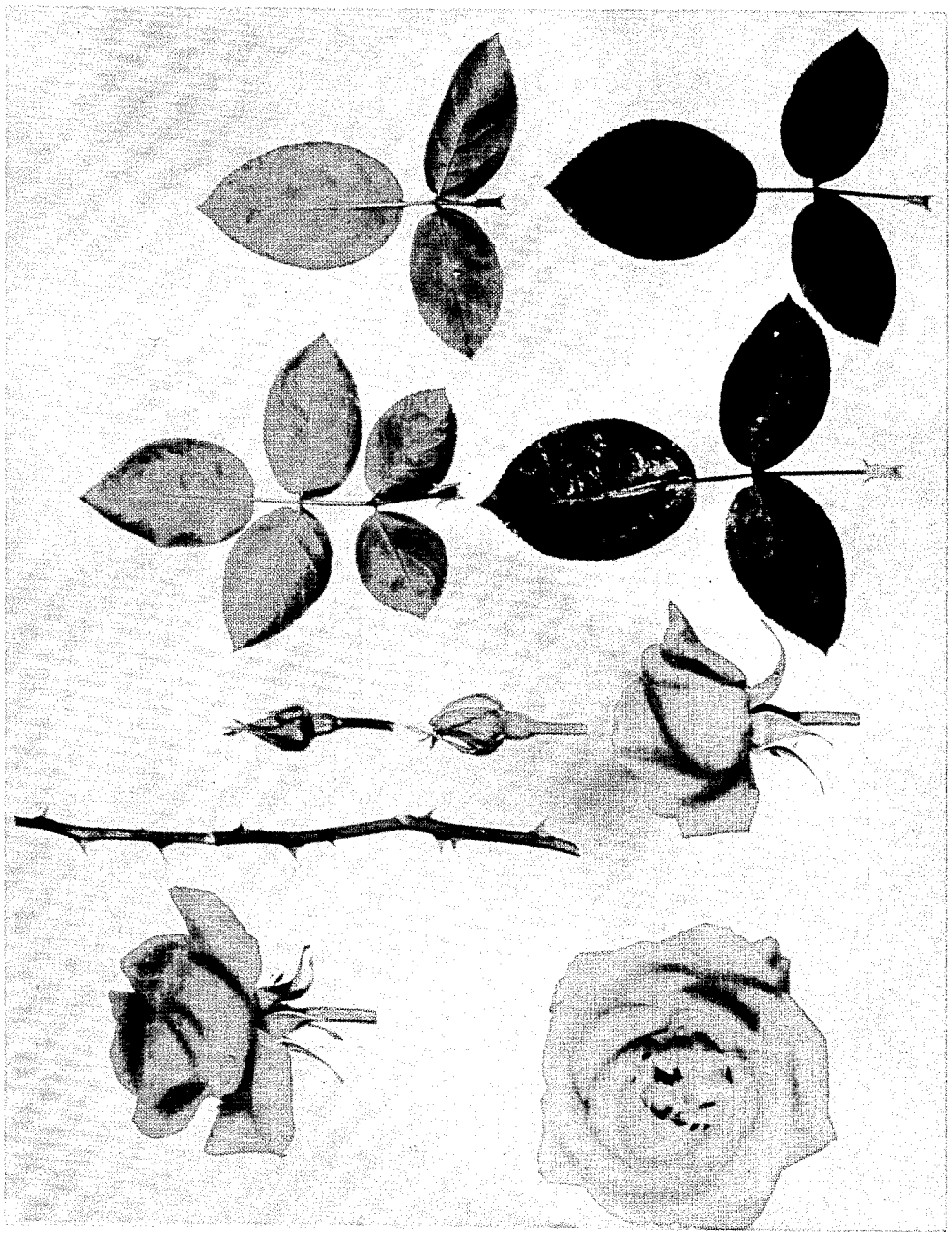
Inventor.
Charles Samtmann
By: Robb & Robb
Attorneys.

United States Patent Office

Plant Pat. 2,545
Patented July 20, 1965

2,545
ROSE PLANT

Charles Samtmann, Philadelphia, Pa., assignor, by mesne assignments, to The Conard-Pyle Company, West Grove, Pa., a corporation of Pennsylvania Filed Apr. 20, 1964, Ser. No. 361,317
1 Claim. (Cl. Plt.—20)

The present invention relates to a new and distinct variety of rose plant of the hybrid tea class, which was discovered by me as a sport of the variety known as "Baccara" (Plant Patent No. 1,367).

At the time of my discovery aforesaid, a bed of the parent variety "Baccara" was being grown under my direction and supervision in a greenhouse on the property of my assignee, located at Wyndmoor, Philadelphia, Pennsylvania. While cutting flowers for the market from this greenhouse bed, my attention was attracted to one plant which bore flowers of a form and color quite different from the normal flowers of the variety "Baccara." Upon close examination of this particular plant, I found that it had sported and I thereupon took steps to preserve the sport, keep it under observation, and to later asexually reproduce the same. My observation of the original plant and the asexual reproductions thereof, as performed by grafting and budding at Wyndmoor, Philadelphia, Pennsylvania, and also at San Jose, California, fully confirmed that the sport was endowed with a unique combination of outstanding characteristics which distinguish the same from the parent variety "Baccara," as well as from all other varieties of which I am aware, as evidenced by the following features:

(1) Moderately large, leathery and attractive foliage which is not as deeply serrated as that of the parent variety;

(2) Distinctly pointed buds of medium length, instead of typical globular buds of the parent variety;

(3) A double flower form and good petalage, with the petal count being slightly less than that of the parent variety;

(4) A distinctive and attractive Turkey Red general color tonality of the flowers, with pronounced underlying orange tones, and the flowers being lightly shaded on the reverse side of the petals with Rose Red and differing from the parent variety by being generally lighter in color; and (5) Good keeping qualities of the flowers as compared with other varieties, and being especially suitable for cut flower production.

The accompanying drawing shows typical specimens of the vegetative growth and flowers of my new variety in different stages of development, as depicted in color as nearly true as it is reasonably possible to make the same in a color illustration of this character.

The following is a detailed description of my new variety, with color terminology in accordance with the Horticultural Color Chart of the Royal Horticultural Society, except where general color terms of ordinary dictionary significance are obvious:

Type: Hardy; bush; outdoor and greenhouse; sport; primarily for cut flowers.
Class: Hybrid tea.
Breeding: Sport. Parent—"Baccara."
Propagation: Holds its distinguishing characteristics through succeeding propagations by budding, and also by grafting.

*Flower*

Locality where grown and observed: London Grove, Pennsylvania.
Flowers Borne: Usually singly to stem; on stems of long length and normal strength.

Quantity of bloom: Free, in greenhouse.
Continuity: Continuous.
Fragrance: Slight. Nature—tea.
Bud:
*Peduncle.*—Medium long; medium caliper; erect; stiff; medium rough; with few green prickles.
*Color.*—Lettuce Green, Plate 861, lightly overlaid with bronze.
*Before calyx breaks.*—Size—medium. Form—medium length; ovoid; with a conspicuous neck; usually without foliaceous appendages on the surface of the bud; with slender bristle-like foliaceous parts extending beyond the tip of the bud equal to ¼ or more of its length.
*As calyx breaks.*—Color—Currant Red, Plate 821.
*As first petal opens.*—Size—medium. Form—medium long; urn shaped. Color: outside—between Delft Rose, Plate 020 and Carmine, Plate 21; inside—near Blood Red, Plate 820.
*Opening.*—Opens up well.
Bloom:
*Size (when fully open).*—Medium large; from 4 inches to 4½ inches.
*Petalage.*—Double; from 40 to 45 petals; arranged regularly.
*Form.*—High-centered at first, but becoming shallow cupped; petals being at first loosely rolled outward and remaining loosely rolled outward at maturity.
Petals:
*Texture.*—Medium thickness; leathery.
*Appearance.*—Inside—velvety. Outside—satiny.
*Shape.*—Outer petals—roundly obovate. Intermediate petals—obovate. Inner petals—obovate, but sometimes irregular; scalloped.

This description of a newly opened flower was made from a rose grown in a greenhouse during the month of March, at London Grove, Pennsylvania:

*Color.*—Outer petal: outside surface—near Cherry, Plate 722, with area surrounding point of attachment Rose Red, Plate 724/3; inside surface—Turkey Red, Plate 721, with an underlying luminescence occasionally streaked with lighter markings of varying and unidentifiable color, and with base of petal surrounding point of attachment near Rose Red, Plate 724/3. Intermediate petal: outside surface—between Cherry, Plate 722/1 and Cherry, Plate 722/2, with area surrounding point of attachment near Rose Red, Plate 724/1; inside surface—Turkey Red, Plate 721/1, with an underlying luminescence which tends to brighten the color, and with area surrounding point of attachment near Rose Red, Plate 724/2. Inner petal: outside surface—Cherry, Plate 722/2, with base of petal near Rose Red, Plate 724/1; inside surface—Turkey Red, Plate 721/1, appearing luminescent when viewed in certain lights, and with base of petal near Rose Red, Plate 724/3.

This description was made from a rose that was open for three days in a greenhouse during the month of March, at London Grove, Pennsylvania:

*Color.*—Outer petal: outside surface—Carmine, Plate 21, with basal quarter of petal Rose Madder, Plate 23/1; inside surface—intermediate between Geranium Lake, Plate 20 and Turkey Red, Plate 721, with base of petal surrounding point of attachment Roseine Purple, Plate 629/1. Point of attachment off-white (unidentified). Inner petal: outside surface—near Carmine, Plate 21/1 becoming progressively overlaid with Rose Madder, Plate 23/1 over basal half of petal; inside surface—near Geranium Lake, Plate 20/1 overlaid surrounding point of attachment with Roseine Purple, Plate 629/2. Point of attachment off-white (unidentified).

*General color effect.*—Newly opened flower—Turkey Red, Plate 721. Three days open—between Geranium Lake, Plate 20 and Turkey Red, Plate 721.

*Behavior.*—Persist.

*Flower longevity.*—Cut roses grown in greenhouse and kept at living room temperature—six days in March.

*Reproductive organs*

Stamens: Medium number; arranged irregularly about pistils; mixed with petaloids.

Filaments: Medium length; most with anthers. Color—Phlox Pink, Plate 625/1.

Anthers: All open at once; medium size; occasionally an anther fused with a petaloid. Color—Chinese Yellow, Plate 606.

Pollen: Moderate quantity. Color—gold.

Pistils: Medium number.

Styles: Uneven; from short to medium length; medium caliper; bunched.

Stigma: Color—white.

Ovaries: All enclosed in receptacle.

Hips: None observed.

Sepals: Permanent; medium length; spear-shaped.

Seeds: None observed.

*Plant*

Foliage:

*Leaves.*—Compound of 3–5 or occasionally 7 leaflets; normal abundance; moderately large; leathery.

*Leaflets.*—Shape—elliptic. Apex—acute. Base—obtuse. Margin—simply serrate.

*Color.*—Mature: upper surface—near Spinach Green, Plate 0960; under surface—Lavender Green, Plate 000761. Young: upper surface—Willow Green, Plate 000862, overlaid with near Garnet Brown, Plate 0023/3; under surface—Willow Green, Plate 000862, heavily overlaid with Garnet Brown, Plate 0023/3.

*Rachis (the supporting stem of the compound leaf).*—Medium caliper. Upper side—grooved; hairy; prickly. Under side—sparsely prickly.

*Stipules.*—Medium length; narrow width; with very short points turning out at an angle of more or less 45°.

*Disease resistance.*—Resistance comparable to the average variety growing under the same cultural conditions at London Grove, Pennsylvania.

Growth:

*Habit.*—Upright; much-branched.

*Growth.*—Free.

*Canes.*—Medium caliper.

*Main stems.*—Dull. Color—Spinach Green, Plate 0960/2. Prickles—many; color—brown. Hairs—none.

*Branches.*—Dull. Color—Spinach Green, Plate 0960/2. Prickles—many; color—greenish brown. Hairs—none.

*New shoots.*—Dull. Color—Lettuce Green, Plate 861/3, with a reddish overcast. Prickles—many; color—reddish. Hairs—none.

I claim:

A new and distinct variety of rose plant of the hybrid tea class, substantially as herein shown and described, characterized particularly as to novelty by the unique combination of moderately large, leathery and attractive foliage, distinctly pointed buds of medium length, a double flower form and good petalage, a distinctive and attractive Turkey Red general color tonality of the flowers, said flowers having pronounced underlying orange tones and being lightly shaded with Rose Red on the reverse side of the petals, and good keeping qualities of the flowers, with special suitability for cut flower production.

No references cited.

ABRAHAM G. STONE, *Primary Examiner.*